United States Patent
Cioca et al.

[11] Patent Number: 6,139,855
[45] Date of Patent: Oct. 31, 2000

[54] STRUCTURED WATER IN COSMETIC COMPOSITIONS

[75] Inventors: Gheorghe Cioca, Lake Grove; Joseph Gubernick, New York; Andrew J. Bevacqua, E. Setauket; Nicolae Vrabie, Jackson Heights; Daniel H. Maes, Huntington; Kenneth D. Marenus, Dix Hills; Edward Pelle, Valley Stream; Neelam Muizzuddin, Bethpage; Vasile Ionita-Manzatu; Mirela Cristina Ionita-Manzatu, both of Old Bethpage, all of N.Y.

[73] Assignee: Color Access, Inc., Melville, N.Y.

[21] Appl. No.: 09/243,362

[22] Filed: Feb. 1, 1999

Related U.S. Application Data

[63] Continuation-in-part of application No. 09/039,113, Mar. 13, 1998, abandoned.

[51] Int. Cl.[7] .................................................... A61K 9/10
[52] U.S. Cl. ...................... 424/401; 424/78.03; 514/937
[58] Field of Search .......................... 424/401, 69, 78.03; 514/937

[56] References Cited

FOREIGN PATENT DOCUMENTS

| | | |
|---|---|---|
| 62-258312 | 11/1987 | Japan . |
| 92060563 | 9/1992 | Japan . |
| 7096282 | 4/1995 | Japan . |
| 7185550 | 7/1995 | Japan . |
| 7277996 | 10/1995 | Japan . |
| 9315925 | 12/1997 | Japan . |
| 107544 | 3/1996 | Romania . |
| 107545 | 3/1996 | Romania . |
| 107546 | 3/1996 | Romania . |
| 90/15779 | 12/1990 | WIPO . |
| 9606048 | 2/1996 | WIPO . |
| 96/32117 | 10/1996 | WIPO . |
| WO96/32117 | 10/1996 | WIPO . |

*Primary Examiner*—Raj Bawa
*Attorney, Agent, or Firm*—Kenyon & Kenyon

[57] ABSTRACT

The invention relates to composition having enhanced biological activity, the compositions comprising at least one structured water. In particular, the compositions contain a combination of I and S waters and a biologically active agent, in which the activity of the agent is increased relative to its activity in a non-structured water composition.

17 Claims, 2 Drawing Sheets

STRUCTURED WATER IN COSMETIC COMPOSITIONS

RELATED APPLICATIONS

This application is a continuation-in-part of U.S. Ser. No. 09/039,113, filed Mar. 13, 1998, now abandoned the contents of which are incorporated herein by reference in their entirety.

FIELD OF THE INVENTION

The present invention relates to aqueous cosmetic compositions. In particular, the invention relates to cosmetic compositions which have improved properties by virtue of the use of structured water.

BACKGROUND OF THE INVENTION

Water is the predominant component of the human body, and in fact of all living things. It is an essential participant in metabolic and synthetic processes in the body. There has been much speculation on how water interacts with cellular components, and many authors have speculated that water may in fact change structure and function once it has been taken into tissues and cells (see, e.g., Benal and Fowler, Trends Biochem. Sci. 8: 1, 1983; Stillinger, Science 209: 4455, 1980; Frank and Wen, Proc. R. Soc. Lond., 1980: A247, 1981; Franks, Water, A Comprehensive Treatise, London, 1981).

In connection with the possible alteration of water's structure, it has been shown (Bernal and Fowler, supra) that an equilibrium exists in water between the $(H_3O)^+$ and $(OH)^-$ structures, in the absence of an ordering electric field. It has been more recently shown (RO 88053/1987; RO 88054/1987; and RO 109835/1995) that if a polarizing electrical field is passed through the water, the equilibrium is destroyed, and the two component ions begin to move independently. Therefore, the generation of this electric field between two electrodes results in a "structuring" process in water, wherein the $R^-H^+_n$ structures, in which $R^-$ represents a polymeric radical, migrates in the direction of the positive electrode, accumulating as "acid water"; similarly, the $R^+(OH)^-_n$ components migrate toward the negative electrode, giving rise to "basic water". Many phenomena may contribute to the structuring of water, and aqueous solutions, including alignment of the dipole moments of water molecules, transport of existing charges in solutions toward the electrodes, magnitude of the applied potential difference, influence of the nature, size and shape of the electrode surface, and $H^+$ and $OH^-$ tunneling. Whatever the influences resulting in structuring, however, the structured (or "activated") water is defined as water that contains stabilized clusters of ions. The acid fraction is alternately referred to as structured water I (or "I water") containing stabilized clusters of $R^+(H)^-(Cl^-, PO_4^{3-}, SO_4^{2-})$ ions. The basic fraction is alternately referred to as structured water S (or "S water") which contains stabilized clusters of R+(OH)-n ($Ca^{2+}$, $Mg^{2+}$, $Na^+$, $K^+$, etc.) ions. To further distinguish the two types of water, I water is characterized by a conductivity $C(\mu S/cm)$ of about 900–2500 and pH of about 1.9–2.5; S water is characterized by a conductivity $C(\mu S/cm)$ of about 400–1500, and a pH of about 10.5–12, each resulting from tap water with $C(\mu S/cm)$ of about 330, and a pH of about 7.4.

Substantial differences are found among the UV spectra of I, S, tap and deionized water, particularly in the 200–250 nm band. When their reactivities are measured in an electronographic field, I, S and tap waters also show significant differences. In particular, for tap water, the total light flux after electronographic stimulation has a positive impulse $I^+$ substantially equivalent to it negative impulse $I^{-'}$. For structured water, the S water stimulated in the same way in positive impulse shows a very high light reactivity, whereas the negative impulse reactivity is almost equivalent to that of distilled water, yielding a positive to negative ratio of greater than 1; in contrast, the reactivity of the I water samples shows a high negative impulse, with a positive impulse approximately equivalent to distilled water, the ratio of positive to negative being less than 1. Different biological properties have been suggested for each type of water. These demonstrated differences in structure between the two types of structured waters have been said to correlate with their biological activities: S water is said to have a stimulatory effect on enzymatic and other biosynthetic processes, whereas I water is said to be inhibitory of the same processes.

Structured water has been disclosed for use in cosmetic compositions previously, in, for example RU 107544, RU 107545 and RU 107546, which relate to the use of I water in specific cosmetic products, for the treatment of oily skin, dry skin, or acne. However, a specific biological effect has not been attributed directly to I water in such compositions. It has now been discovered that the use of different structured waters can have beneficial effects on the performance of actives in compositions for topical application to the skin.

SUMMARY OF THE INVENTION

The present invention relates to cosmetic and pharmaceutical compositions for topical application to the skin, comprising activating effective amounts of a combination of I and S water, in combination with a biologically active agent. In particular, it has been found that the combination of S and I water, in proportions that are appropriate to the polarity of the active, or the medium in which the active is contained, can enhance the performance of a biological active in a topically applied composition. The invention also relates to a method for enhancing the activity of a biological active comprising formulating the active with polarity-appropriate amounts of I and S water.

DETAILED DESCRIPTION OF THE INVENTION

Figure 1:
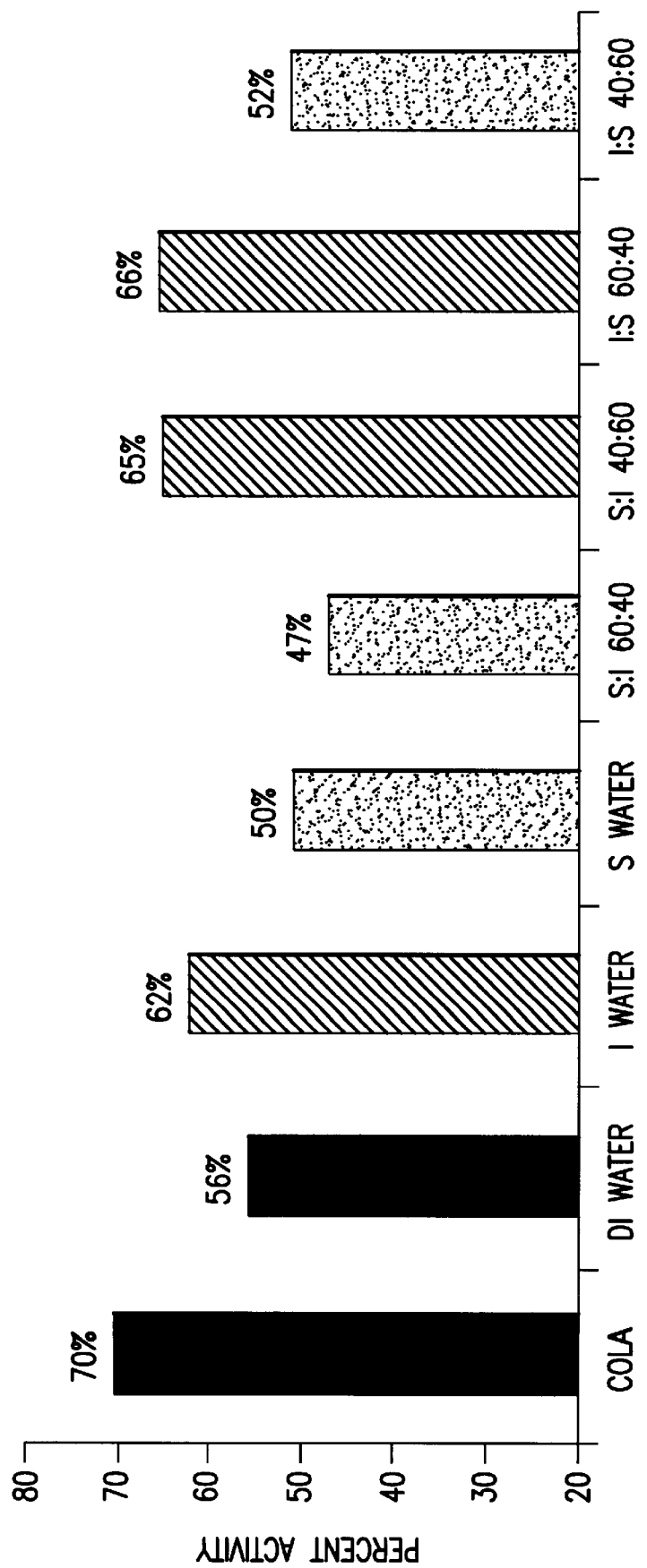
FIG. 1 illustrates the anti-irritancy effect of caffeine (cola) in premixed combinations of S and I water.

As noted above, structured water and methods for making same are well known in the art. For example, RO 88053 describes a method for producing "B" or basic (S-type) water, and RO 88054 discloses a method for making "A" or acid (I-type) water. Improvements in making either of these types of water are further described in WO 9606048. The contents of each of these documents is incorporated herein by reference.

It has been now been discovered that a combination of I water and S water is unexpectedly effective in increasing the efficacy of a biological active in a cosmetic or pharmaceutical topical composition. In experiments comparing the results obtained when an active is placed in different vehicles, such as deionized water, or I water or S water alone, with those obtained with the combined I and S waters, the combination of I and S shows a higher level biological activity for the pertinent active than does any of the single vehicles tested under the same conditions; however, I water itself also shows a considerable level of activity enhancement as well, and S water shows enhancement of certain types of activity, namely antioxidant activity. This result has been observed with materials of very distinct chemical identity and biological activity, for example, an anti-irritant such as caffeine, and an antioxidant such as BHT.

A particularly effective enhancement is observed when the I and S waters are combined in proportions which reflect the relative positively and negatively charged components of the active to be enhanced. More specifically, the amounts of I water and S water in any given formulation are preferably selected to reflect the polar composition of the active. The relative charge of the components of any given active can readily be determined by simple electrophoretic analysis. Positive components of the active will migrate to the negative pole, and negative components will migrate to the positive pole. The relative proportions of each are then determined, and based on this, the effective amounts of I and S water concentrations to be used are calculated. For example, in a composition with a predominantly positive charge, the structured water composition should be predominantly I water. Preferably, the amount of I water is substantially matched to the proportion of positive component, and the amount of S water substatially matched to the proportion of negative component. As a specific example, an active containing 60% positive component, and 40% negative component would be most effectively enhanced in a combination of I and S water in a ratio of about 60% I water: about 40% S water. The ratios are preferably matched substantially exactly, but some variation is possible. Generally, it is preferred that the amount of I or S water not vary from its corresponding component's proportion by a factor of more than about ±10%, preferably no more than about ±5%, more preferably no more than about ±2%. This analysis can be applied not only to an individual active, but also to the collected components of an aqueous phase of a proposed composition.

The structured water combination can be used in any topically applied skin care product in which there is an aqueous component. For example, the structured water can be employed in a purely aqueous vehicle, a hydroalcoholic vehicle, or as part of the aqueous phase of a water-in-oil or oil-in-water emulsion. The form the vehicle takes can be any which is suitable for topical application to the skin, for example, solutions, colloidal dispersions, emulsions, suspensions, creams, lotions, gels, foams, mousses, sprays and the like.

The type of active, the activity of which is enhanced by the presence of I and S water, can be any which is beneficially used in a skin care product. For example, the structured water is useful in enhancing the moisturization properties of a moisturizing composition containing moisturizing actives. The combination can also be used to enhance the activity of agents used to treat age spots, keratoses and wrinkles, as well as analgesics, anesthetics, anti-acne agents, antibacterials, antiyeast agents, antifungal agents, antioxidants, antiviral agents, antidandruff agents, antidermatitis agents, antipruritic agents, antiemetics, antimotion sickness agents, anti-irritant agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, sunscreen agents, antihistamine agents, skin lightening agents, depigmenting agents, wound-healing agents, vitamins, corticosteroids, self-tanning agents, or hormones. The I/S water combination can be used in an amount of from about 1 to about 99.5% by weight of the composition as a whole, but more frequently will be used at levels of from about 20–80%, more preferably from about 40–80%. The combination itself can constitute the entire aqueous component of the composition. Alternately, the I and S combination can be a portion of the aqueous component, i.e., further combined with other non-structured aqueous components, such as distilled water, or a floral water. The use of non-structured water with structured water is possible, since the enhancing effect of the I/S combination has been observed even at dilutions of 1/1000.

The structured waters can be used in virtually any type of skin care product which has an aqueous component. For example, it can be used to enhance the properties of actives used in makeup products, such as lipsticks and glosses, foundations, blushes, eyeliners, eyeshadows and the like. It will also be useful in treatment products, including pharmaceutical products, in which the efficacy of biologically active components is particularly crucial.

The following non-limiting examples illustrate the invention.

EXAMPLES

Example I

This example illustrates the determination of polarity of an active, and its application to combination with I and S water.

Samples to be analyzed are dissolved in deionized water, up to a concentration of 20%. The solutions are mixed in a ratio of 1:1(v/v) with a 0.2% solution of $AgNO_3$, so that all test samples contain the same quantity of silver. Samples should be tested immediately, to prevent silver precipitation.

High Resolution Buffer (product no. 51104 by Gelman Products, sold by VWR Scientific Products) is used as the stationary buffer in electrophoresis. The High Resolution Buffer is diluted in deionized water 15 times more than the standard dilution recommended by the vendor. The electrophoresis equipment employed is a Semi-Micro II Chamber (product no. 51214 by Gelman Sciences, sold by VWR Scientific Products); EC500-90 power supply (E-C Apparatus Corporation, Holbrook, N.Y.); and Sepraphore III microporous cellulose acetate membrane (product no. 62092 by Gelman Sciences, sold by VWR Scientific Products).

The electrophoresis chamber is filled with 200 ml of buffer (100 ml each side). The partition should be free from buffer solution droplets. 100 ml is also placed in a staining tray. The membrane is removed from the package, its midpoint marked with a pencil, and floated on the surface of the buffer in the tray to wet it completely. It is then submerged and soaked for 10 minutes. The membrane is removed and placed on an absorbent pad, and blotted with another absorbent pad. The membrane is then placed on the bridge of the electrophoresis chamber, and a volume of 5 μl of each sample, plus the control, is pipetted onto the membrane on the midpoint line. Power is turned on, at a voltage in the range of 50–120V, with a migration time of 30 minutes.

The migration distance of silver nitrate (0.1%), which is entirely toward the negative pole, is taken as the control. A sample that migrates the same distance, in the same direction, as the silver control, is non-polar. A sample migrating a greater distance, in the same direction as the control is considered 100% positively charged. A sample migrating in both directions has two components, that migrating in the direction of the silver being the positive component, and that migrating in the opposite direction the negative component.

To determine the proportion of the sample which is positive, and which is negative, the migration distances are measured. The migration distance of the positively charged component is designated $X^+$, and that of the negatively charged component, $X^-$, the total migration distance being $X^+ + X^-$. $X^-$ represents a number equal to $X^-/X^+ + X^-$ (fraction a), and $X^+$ represents a number equal to $X^+/X^+ + X^-$ (fraction b). These numbers are used to determine the best ratio for I and S water.

As a general example, for a 100% positively charged sample, the sample is combined with 100% I water. If a>b, the sample is negatively charged, and the optimal ration to be used is aS %+bI %; if a<b, the sample is positively charged, and the optimal ratio is aI %+bS %,. If a=0, the sample is negatively charged, and the sample is combined with 100% S water. The activity and stability of a non-polar sample is not influenced by the influence of other charges, and will not benefit significantly from combination with I and S water. Thus, such non-polar samples may be combined equally well with deionized water, I water and S water, in any proportion and combination.

In a specific example, the polarity of caffeine, an anti-irritant, is measured by this method. The a %, $X^-/X^+ + X^- = 7/17 = 42\%$; the b % is $X^+/X^+ + X^- = 10/17 = 58\%$.

Example II

This example illustrates the enhancement of anti-irritant activity of caffeine in the presence of a combination of I and S water.

Caffeine is added at a level of 0.5%, to a series of different vehicles, as follows:

1. 100% deionized water, pH 6.98
2. 100% I water, pH 2.60
3. 100% S water, pH 9.60
4. S water added to I water, S:I, pH 3.42
5. S water added to I water, S:I 40:60, pH 3.06
6. I water added to S water, I:S 60:40, pH 2.81
7. I water added to S water, I:S 40:60, pH 3.31

Seven volunteers with a history of skin sensitivity to Balsam of Peru are chosen for the study. The test compounds are applied on the ventral forearms of the panelists. The material is allowed to absorb for twenty minutes and then Balsam of Peru, an irritant, is applied on the test sites. Skin irritation is measured in terms of increase in skin redness. The degree of redness is measured with the Minolta Chromameter and compared with the positive and negative controls. The positive control is the color of skin treated with Balsam of Peru alone, and the negative control is a skin site treated with a 10% hydroalcoholic cola nitida solution and challenged like the test products. The results are summarized in FIG. 1. As the figure shows, caffeine in I water is 62% active, compared with only 56% activity of caffeine in deionized water. Even better results are seen, however, with the combination of I and S water, particularly for the combination in which I water predominates in a 60:40 ratio.

Example III

This example illustrates the enhancement of antioxidant activity seen in the combination with I and S water.

The activity of the antioxidant BHT in the presence of various aqueous components is tested by evaluation of its efficacy in a UV-induced lipid peroxidation reaction in vitro. Phosphate buffered saline(PBS) is first prepared in either distilled water, S water, I water, and mixtures of 40/60 combinations of I and S waters. Phosphatidyl choline in ethanol is then injected into the PBS solutions to form liposomes and these are used as controls. The test samples are prepared by pre-mixing phosphatidyl choline and BHT, and then injecting them into one of the respective PBS solutions. In order to detect differences among the solutions, the final concentration of BHT is titrated down to 0.003%. After liposome preparation, the samples are exposed to UVC radiation for two hours followed by determination of thiobarbituric acid-reacting substances which indicates the extent of lipid peroxidation. From these data, the percent inhibition of peroxidation by BHT is calculated. The experiments at 0.003% BHT are done four times in duplicate.

Figure 2:
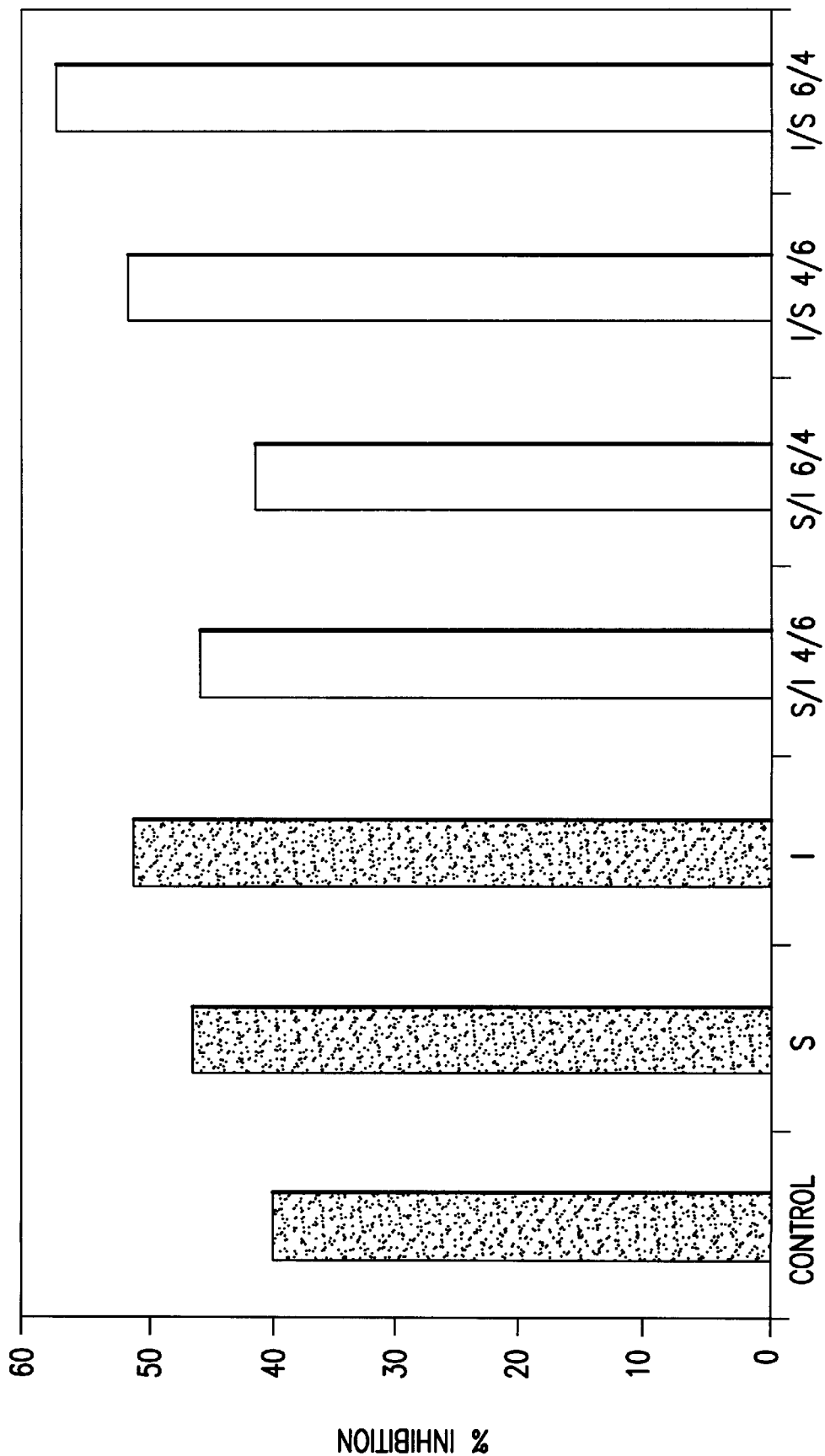
FIG. 2 illustrates the average % inhibition of UV-induced peroxidation by BHT in distilled, S and I waters, and 60/40 combinations of S and I waters.

Results of the activity of BHT in combination with a single water type, as well as combinations are shown in FIG. 2. The average value of BHT alone in distilled water is about 40%; in the presence of S water, the inhibition increases to about 47%, and while with I water, this increases to over 51%. A two tailed t-test shows there is statistical difference of $p<0.052$ between distilled and S water, and $p<0.045$ between distilled and I water. The samples in which the combination of I and S waters are used show a similar increase in BHT activity, particularly in the case in which I water is added to S water in a ratio of 60:40.

To eliminate the possibility that the pH of I water, which is acidic, is responsible for the inhibition by reducing the pH of PBS to 6.3, the pH of PBS in distilled water is titrated to pH 6.3, and used in the same assay. The results of this assay indicate that there is no difference attributable to pH under such conditions. Also, the pre-separation (i.e., pre-electrolysis) water is also run as a control, and no enhancement of BHT activity is seen.

What we claim is:

1. A cosmetic or pharmaceutical composition for topical application to the skin, the composition containing a structured water component comprising a combination of I and S water, wherein I water is characterized by a conductivity of about 500–3000 $\mu$S and pH of about 2.0–3.0; S water is characterized by a conductivity of about 600–2500 $\mu$S, and a pH of about 10–12, each resulting from starting water with $\mu$S/cm of about 250–450, and a pH of about 7–7.5.

2. The composition of claim 1 which also comprises a biologically active agent.

3. The composition of claim 2 in which the active agent has a predominantly positive charge.

4. The composition of claim 3 in which I water is present in an amount of greater than 50% of total structured water.

5. The composition of claim 2 in which the active agent has a predominantly negative charge.

6. The composition of claim 5 in which S water is present in an amount of greater than 50% of total structured water.

7. The composition of claim 2 in which the biologically active agent is an anti-irritant agent.

8. The composition of claim 2 in which the biologically active agent is an antioxidant.

9. The composition of claim 1 which is a moisturizing composition.

10. A method of increasing the activity of a biologically active agent in a topically applied composition which comprises combining the agent with a polarity-appropriate percentage of I water, S water or a combination thereof, wherein I water is characterized by a conductivity of about 500–3000

μS and pH of about 2.0–3.0; S water is characterized by a conductivity of about 600–2500 μS, and a pH of about 10–12, each resulting from starting water with μS/cm of about 250–450, and a pH of about 7–7.5.

11. The method of claim 10 in which the active agent has a predominantly positive charge.

12. The method of claim 11 in which I water is present in an amount of greater than 50% of total structured water.

13. The method of claim 10 in which the active agent has a predominantly negative charge.

14. The method of claim 13 in which S water is present in an amount of greater than 50% of total structured water.

15. The method of claim 10 in which the biologically active agent is an anti-irritant agent.

16. The method of claim 10 in which the biologically active agent is an antioxidant.

17. The method of claim 10 which is a moisturizing composition.

* * * * *